(12) United States Patent
Habrovec et al.

(10) Patent No.: US 7,645,429 B2
(45) Date of Patent: Jan. 12, 2010

(54) JACKET OF A STEAM STERILIZER CHAMBER

(75) Inventors: Michal Habrovec, Brno (CZ); Ivan Hodan, Brno (CZ); Milan Krajcar, Brno (CZ)

(73) Assignee: BMT Medical Technology S.R.O. (CZ)

( * ) Notice: Subject to any disclaimer, the term of this patent is extended or adjusted under 35 U.S.C. 154(b) by 294 days.

(21) Appl. No.: 11/569,962

(22) PCT Filed: Jul. 4, 2005

(86) PCT No.: PCT/CZ2005/000054

§ 371 (c)(1),
(2), (4) Date: Dec. 2, 2006

(87) PCT Pub. No.: WO2006/005270

PCT Pub. Date: Jan. 19, 2006

(65) Prior Publication Data

US 2008/0206119 A1    Aug. 28, 2008

(30) Foreign Application Priority Data

Jul. 8, 2004    (CZ) ............................ PV 2004-793

(51) Int. Cl.
*A61L 2/07* (2006.01)
(52) U.S. Cl. ............................ 422/295; 422/26; 422/33

(58) Field of Classification Search ............... 422/26, 422/33, 295
See application file for complete search history.

(56) References Cited

U.S. PATENT DOCUMENTS 2,526,974 A * 10/1950 Schipanski ................. 422/106
3,674,981 A * 7/1972 Pickard ..................... 219/401
5,666,878 A    9/1997 Taricco

FOREIGN PATENT DOCUMENTS

WO    2001-58498 A1    8/2001

* cited by examiner

*Primary Examiner*—Sean E Conley
(74) *Attorney, Agent, or Firm*—Oppedahl Patent Law Firm LLC

(57) ABSTRACT

A jacket of a steam sterilizer embedding a sterilization chamber (3) consisting of two separated and independent each other parts of which a heating part (1) of the jacket embeds the sterilization chamber (3) while a filling part (2) of the jacket is advantageously arranged in the bottom part of the sterilization chamber (3), said parts form the integral unit. Both the outlet of a first steam filling valve (4) and the inlet of a first pressure sensor (5) enter the heating part (1), and both the outlet of a steam filling valve (6) and the inlet of a second pressure sensor (7) and the inlet of a third steam filling valve (8) enter the sterilizing chamber (3) into which both the outlet of the third steam filling valve (8) and the inlet of a third pressure sensor (9) enter, enter the area of the filling part (2).

5 Claims, 4 Drawing Sheets

JACKET OF A STEAM STERILIZER CHAMBER

FIELD OF THE INVENTION

The present invention relates to a jacket of a steam sterilizer chamber, particularly optimization of the physical environment in said chamber of the steam sterilizer using a divided jacket of the chamber.

STATE OF THE ART

Steam supply into a sterilization chamber of large-sized steam sterilizers has been so far solved so that steam is first supplied into a jacket of the sterilization chamber of the sterilizer, which is thereby pre-heated. Steam is then supplied through a filling valve into the sterilization chamber. All steam intended for filling of said sterilization chamber thus flows through the jacket of the sterilization chamber. When steam flows through the jacket, a large part of excess humidity is removed from it, or possible preheating of steam supplied is partially reduced in the jacket. Jacket preheating is the desirable effect that has, nevertheless, its practical limitations. According to the demand, the jacket of the sterilization chamber should have the defined temperature in order to isolate the chamber from surrounding environment. This affects positively not only temperature development in time and its fluctuation, but also temperature distribution within the chamber and within sterilized material. The jacket being heated in this manner supports also significantly good drying effect of the steam sterilizer. High requirements are lately posed on quality of the parameters mentioned above. On the other hand, excessive temperature in the jacket results in the more intensive heat transfer into the sterilization chamber in a parasitic way introducing a disturbance variable into the regulation process occurring in the chamber. The requirements demanding that temperatures measured in the sterilizer chamber shall be within the specified range of the sterilization temperatures of 3K during the maintenance period shall be particularly met. In addition, said measured temperatures shall not vary by more than 1 K and shall not differ from one another in any point by more than 2 K. The time interval between the moments when the sterilization temperature is reached in the coldest and the hottest parts of the sterilizer chamber shall not exceed 15 seconds and 30 seconds for the sterilizer with the sterilization chamber volumes of maximum 800 l and above, respectively.

Considering the requirements for the parameters of heat distribution in the sterilizer chamber and in the sterilized material described above, pressure in the jacket of the sterilization chamber has been currently controlled based on the instantaneous pressure in the sterilization chamber. Steam source intended for supplying of the sterilization chamber is thus affected reversely by the steam pressure in said chamber. The disadvantage of the conditions described above consists in the fact that problems occur in trying to maintain the temperature profile in the empty sterilization chamber of the steam sterilizer. Temperature in the chamber should be measured simultaneously at many points within the chamber, essentially within its entire volume. The temperature difference between the individual points measured at the beginning of the period of maintenance of the sterilization temperature does not obviously meet the standard requirements. Keeping the demanded time interval between the moments when the sterilization temperature is reached in the hottest and coldest parts of the chamber seems to be also problematic.

Temperature non-homogeneities and temperature rise at the phase when steam is supplied into the sterilization chamber are mainly caused—according to the laws of thermodynamics—by quick gas compression occurring in the sterilization chamber. The additional heating thus occurs in the chamber because the excess heat cannot be removed in time into the chamber walls or into the material—the sterilized load. Another disturbance variable for the regulation thus appears. The nature of the variable mentioned seems to be unpredictable; it depends, among others, also on the volume and material of the sterilized subjects, which are unknown beforehand. The problems mentioned above may be solved if the steam filling rate into the chamber is affected.

Nevertheless, only the fixed reduction of the speed of the pressure increase is not capable to react to the different conditions in steam consumption during the different preheating levels in the chamber, to different size and to temperature capacity of the sterilizer load. More intensive steam condensation and larger removal of heat energy supplied occurs in the cold chamber in comparison with the chamber already pre-heated during the previous operation. The similar can be stated for the full chamber in contrast to the empty one.

CZ patent No. 291578 describes the method of steam supply that is capable to react to the actual conditions in the sterilization chamber of the steam sterilizer, size of its load and its heat capacity. This method of steam supply into the sterilizer chamber of the steam sterilizer consists in that it is performed in phases using the direct control of steam pressure increase in the sterilization chamber of the steam sterilizer or by the control of steam pressure increase in the sterilization chamber of the steam sterilizer using the control of the pressure difference, $\Delta p$, between the jacket and the sterilization chamber. The differences between the pressure in the chamber and the pressure of the supplied steam are thus minimized.

Certain disadvantage of the known technical solutions according to which steam is supplied into the sterilization chamber through a heating jacket of the sterilization chamber consists in that the instantaneous pressure in the jacket and thus the instantaneous temperature of the jacket shall be higher than the instantaneous pressure and temperature in the chamber. If this condition fails, steam will not enter the sterilization chamber of the sterilizer. For optimization of the environment in the sterilizer chamber, the jacket temperature shall be lower than the temperature in the sterilization chamber during some phases of the sterilization cycle. This is not feasible in the current design of the jacket of the steam sterilizer. Similarly, it is desirable that the pressure of the steam intended for entry into the sterilization chamber is higher in some phases of the sterilization cycle than can be actually reached with the current arrangement of the jacket of the steam sterilizer. The requirements posed to the pressure in the jacket and its development during the sterilization cycle or to the jacket temperature differ from those ones posed to the pressure or temperature of steam supplied into the sterilization chamber. Current arrangement of both the sterilization chamber and the jacket of the steam sterilizer fails taking in consideration the requirements as mentioned above.

It is therefore an object of the present invention to create such arrangement of the sterilization chamber and the jacket of the steam sterilizer enabling relative independent setting of the optimal physical conditions in the sterilizer jacket, on one hand, and the optimal physical properties of steam intended for the sterilization itself in the chamber of the steam sterilizer, on the other hand. Said arrangement enables the independent control of pressure development during the sterilization cycle in both parts of the divided jacket of the sterilization chamber, which results in improved sterilization process in the steam sterilizer.

SUMMARY OF THE INVENTION

The disadvantages as mentioned above are solved by the arrangement of the jacket of the steam sterilizer chamber embedding the chamber which gist consists in that it includes a heating part of the jacket and a filling part of the jacket, said parts being separated and independent each other.

The main advantage consists in the fact that the jacket divided into two separate and independent parts solves the matter of the contradictory requirements relating to pressure in contrast to the undivided jacket of the steam sterilizer. The chamber of the steam sterilizer is desirably heated with steam flowing in the divided jacket of the steam sterilizer without being overheated as in the case when the higher pressure shall be maintained in the undivided jacket in order to keep steam flow into the chamber.

In order to maintain the defined temperature in the jacket of the steam sterilizer chamber, the heating part of the jacket advantageously embeds the sterilization chamber while the filling part of the jacket is arranged in the bottom part of the sterilization chamber and said both parts form the integral unit; in addition, both the outlet of the first steam filling valve and the inlet of the first pressure sensor enter the heating part of the jacket, and both the outlet of the steam filling valve and the inlet of the second pressure sensor and the inlet of the third steam filling valve into the sterilization chamber into which both the outlet of the third steam filling valve and the inlet of the third pressure sensor enter the area of the filling part of the jacket.

The designed arrangement of the divided jacket of the steam sterilizer according to this invention advantageously enables setting of the optimal pressure or temperature conditions during the sterilization cycle, namely, separately for the heating part of the jacket of the steam sterilizer and separately for the filling part of the jacket of the steam sterilizer where the latter being intended for steam supply into the sterilization chamber itself, and all functions being performed in dependency on the actual phase of the currently running sterilization cycle.

In order to affect positively quality of the sterilization cycle itself, the steam pressure has advantageously the different course in the heating part and the filling part. Said steam filling method can affect positively humidity in the environment of the sterilizer chamber, the temperature conditions and the temperature profile within the chamber, dynamics of both the temperature a pressure changes, dynamics and the total time of the sterilization cycle.

Higher steam pressure in the filling part of the jacket reduces excessive humidity of steam entering the sterilization chamber whereas the lower pressure of the steam in the heating part of the jacket enables creation of the optimal conditions necessary for trouble-free control of the desired temperature profile within the sterilization chamber, both during the sterilization exposure itself and during the pressure rise in the sterilization chamber, particularly during the critical starting phase of the sterilization exposure.

The indispensable advantage consists in that the divided jacket enables on demand utilization of the lower-quality (heating) steam to supply the heating part of the steam sterilizer jacket and thus reducing the consumption of the pure medicinal steam intended for the sterilization itself.

The solution according to this invention enables effective control of the entire sterilization process together with the optimal setting of parameters for the individual, particularly specialized, sterilization programs.

BRIEF DESCRIPTION OF THE FIGURES ON DRAWINGS

For the better understanding of the present invention the references are made to the following drawings where FIG. 1 is a diagram of an arrangement of a sterilization chamber and a divided jacket of a steam sterilizer;

DESCRIPTION OF THE EXEMPLARY EMBODIMENT

An example given is an exemplary variant of the embodiment of this invention that need not be limited to it from the protection point of view.

In order to optimize environment in a sterilizer chamber, steam pressure or temperature in a jacket of a steam sterilizer shall be lower that that in a sterilization chamber 3 in certain phases of the sterilization cycle. The requirement mentioned can be met so that the jacket of the sterilization chamber 3 is divided into a heating part 1 and a filling part 2. The development of pressures $P_{ster}$, $P_1$ and $P_2$ will be therefore different in each inside area of the parts as mentioned above being the constituent part of the steam sterilizer. For example, the steam pressure $P_{ster}$, in the chamber 3 of the steam sterilizer is higher than the steam pressure $P_1$ in the heating part 1 of the jacket of the steam sterilizer during the exposure. At the same time, the steam pressure $P_2$ in the filling part 2 of the jacket of the steam sterilizer is lower during the venting phase than the pressure $P_1$ in the heating part 1 of the jacket of the steam sterilizer, whereas, during the filling and exposure phases, the pressure $P_2$ in the filling part 2 of the steam sterilizer is—on the contrary—higher. At the same time, particularly the pressure or temperature differences of the supplied steam during the sterilization cycle enable the trouble-free supply of the steam into the chamber 3 of the steam sterilizer and thus meeting the required parameters.

Figure 1:
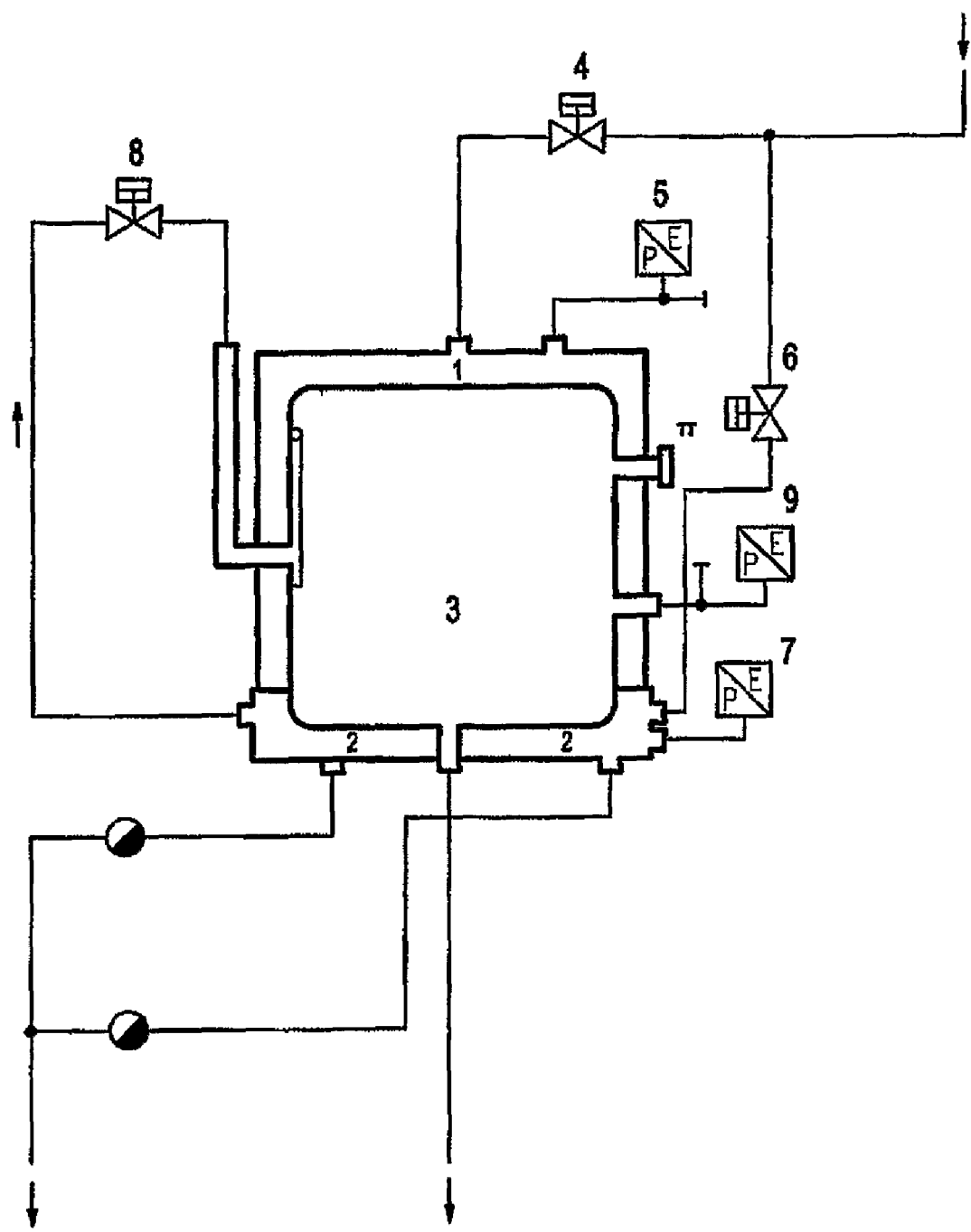
Figure 2:
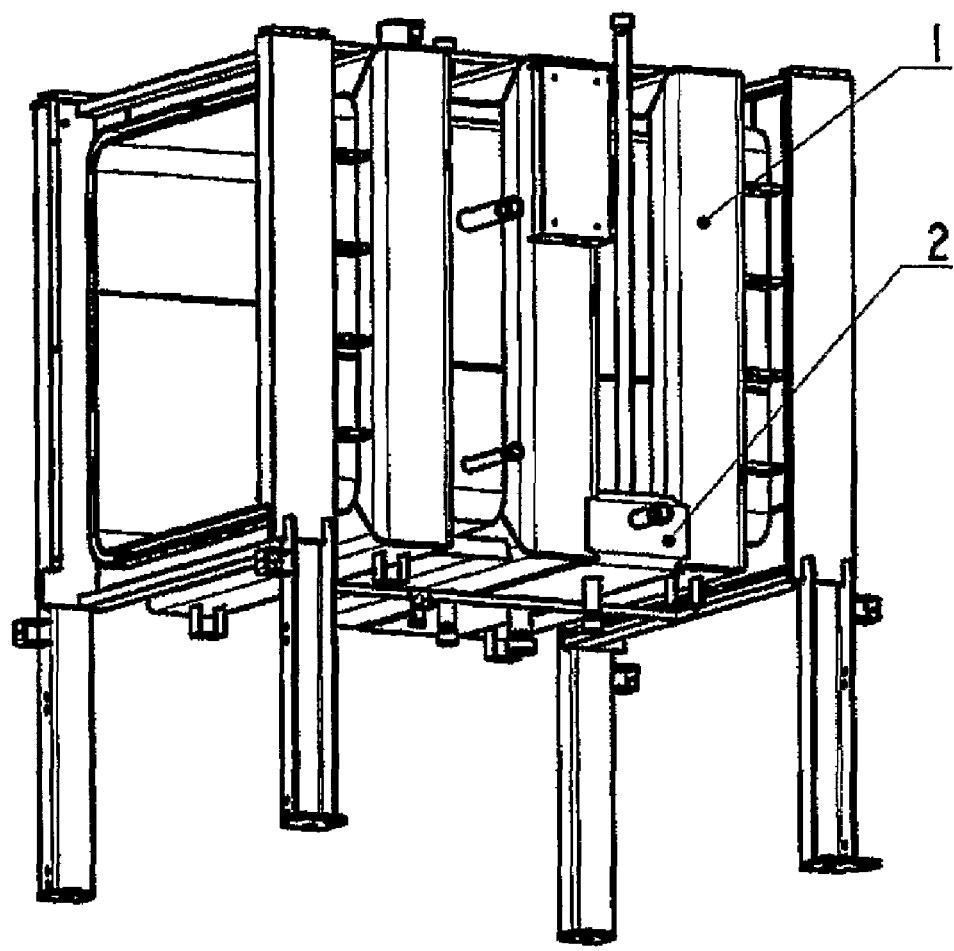
FIG. 2 is the exemplary embodiment of the sterilization chamber with the divided jacket of the steam sterilizer.
Figure 3:
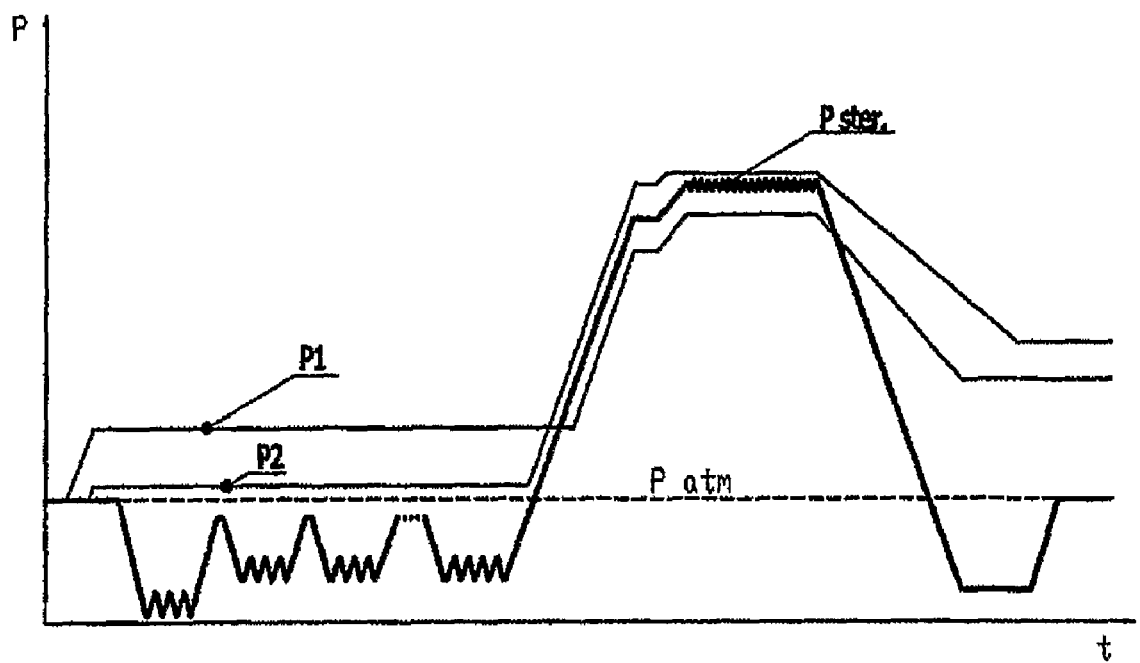
FIG. 3 is the description of developments of pressures $P_{ster}$, $P_1$, and $P_2$ in the chamber, a heating part and a filling part during the sterilization process.

Referring to FIGS. 1 and 2, the sterilization chamber 3 of the steam sterilizer is embedded with the larger, heating, part 1 of the steam sterilizer jacket while the smaller, filling, part 2 of the steam sterilizer jacket is advantageously arranged onto the sterilization chamber 3 in its bottom part; both the heating part 1 and the filling part 2 of the steam sterilizer jacket form the permanent integral unit. Both the outlet of a first steam filling valve 4 and the outlet of a pressure sensor 5 enter the area of the heating part 1 of the jacket. Both the outlet of a steam filling valve 6 entering the jacket and the inlet of a pressure sensor 7 and the inlet of a steam filling valve 8 filling the sterilization chamber 3 of the steam sterilizer enter the area of the filling part 2 of the steam sterilizer jacket. On the other hand, both the outlet of the steam filling valve 8 and the inlet of a pressure sensor 9 enter the area of the sterilization chamber 3.

The function of the steam sterilizer jacket comprising two separated and independent each other parts consists in that steam flows through the steam filling valve 4 into the heating part 1 of the steam sterilizer jacket intended for heating. Pressure in the heating part 1 of the steam sterilizer jacket is scanned by the separate pressure sensor 5. Pressure or temperature in the heating part 1 of the steam sterilizer jacket can be controlled during the sterilization cycle so that it is optimal for the temperature distribution within the sterilization chamber 3 of the steam sterilizer, drying etc. Pressure in the heating part 1 of the steam sterilizer jacket can be controlled independently on the instantaneous pressure in the sterilization chamber 3. Steam flows separately through the steam filling valve 6 into the filling part 2 of the steam sterilizer jacket. The filling part 2 of the steam sterilizer jacket is intended particularly for buffering. Steam parameters, particularly pressure, are there adjusted to the values being optimal for entering into the sterilization chamber 3 of the steam sterilizer during the sterilization cycle. In addition, the filling part 2 of the jacket is also partially intended for heating. Pressure in the filling part 2 of the jacket is scanned by the pressure sensor 7. Steam flows from the filling part 2 of the steam sterilizer jacket through the filling valve 8 into the sterilization chamber 3. Pressure in the sterilization chamber 3 is scanned by the pressure sensor 9.

Figure 4:
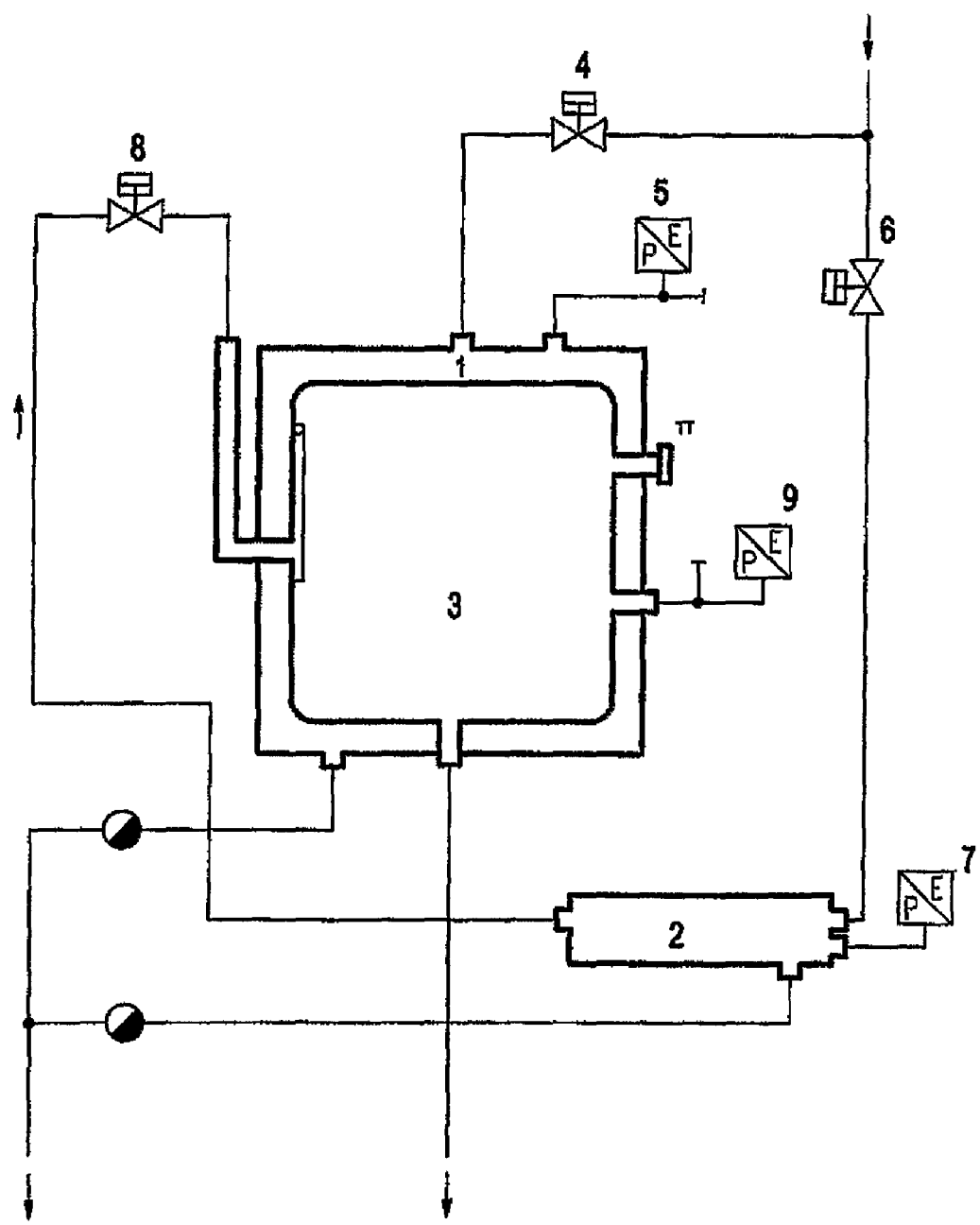
FIG. 4 is the exemplary embodiment of the sterilization chamber with the divided jacket of the steam sterilizer where the filling part does not form the constituent part of the jacket of the steam sterilizer.

The exemplary embodiment of the sterilization chamber with the divided jacket of the steam sterilizer where the filling part does not form the integral part of the steam sterilizer jacket is depicted in FIG. 4. In the case mentioned, the sterilization chamber 3 of the steam sterilizer is again embedded with the larger, heating, part 1 of the steam sterilizer jacket while the smaller, filling, part 2 of the steam sterilizer jacket is arranged outside the steam sterilizer jacket. Both the outlet of the first steam filling valve 4 and the inlet of the pressure sensor 5 enter the area of the heating part 1 of the jacket. Both the outlet of the steam filling valve 6 entering the jacket and the inlet of the pressure sensor 7 and the inlet of the steam filling valve 8 filling the sterilization chamber 3 of the steam sterilizer enter the area of the filling part 2 of the steam sterilizer. On the other hand, both the outlet of the filling valve 8 and the inlet of the pressure sensor 9 enter the area of the sterilization chamber 3.

The function of the steam sterilizer jacket being formed with two separated and independent each other parts is in the case mentioned above identical with that one described in the exemplary embodiment as above.

INDUSTRIAL APPLICABILITY

The divided jacket of the steam sterilizer chamber according to this invention can be used for all types of steam sterilizers.

LIST OF THE REFERENCE CHARACTERS

1—Heating part of the jacket
2—Filling part of the jacket
3—Sterilization chamber
4—Filling valve of the first part of the jacket
5—The first pressure sensor
6—Filling valve of the second part of the jacket
7—The second pressure sensor
8—Steam filling valve
9—The third pressure sensor of the chamber

The invention claimed is:

1. A steam sterilizer jacket embedding a sterilization chamber, the sterilization chamber having a bottom part, characterized in that said steam stabilizer jacket comprises a heating part of the jacket and a filling part of the jacket, which are separated and independent each other, the filling part of the jacket having an area, characterized in that the heating part of the jacket embeds the sterilization chamber while the filling part of the jacket is arranged in the bottom part of the sterilization chamber, said heating part and said filling part of the jacket form an integral unit, and both an outlet of a first steam filling valve and an inlet of a first pressure sensor enter the heating part of the jacket, while both an outlet of a second steam filling valve and an inlet of a second pressure sensor and an inlet of a third steam filling valve enter the sterilization chamber into which both an outlet of the third steam filling valve and an inlet of a third pressure sensor enter, enter the area of the filling part of the jacket.

2. The steam sterilizer jacket embedding the sterilization chamber according to claim 1 characterized in that steam pressure in the heating part has a respective course, and the steam pressure in the filling part has a respective course, and the respective course of the steam pressure in the heating part is different from the respective course of the steam pressure in the filling part.

3. The steam sterilizer jacket embedding the sterilization chamber according to claim 1, characterized in that a steam source of a lower quality is used for feeding of the inlet of the first steam filling valve of the heating part of the jacket, while a source of medicinal steam is used for feeding of the inlet of the second steam filling valve of the filling part of the jacket.

4. A steam sterilizer jacket embedding a sterilization chamber comprising separated parts, the sterilization chamber having a bottom part, the sterilization chamber defining a respective steam pressure, characterized in that the jacket comprises two independently pressure controlled parts, namely a heating part and a filling part, the filling part defining a respective steam pressure and the heating part defining a respective steam pressure, whereas the heating part embeds the sterilization chamber, while the filling part is arranged in the bottom part of the sterilization chamber, said both parts of the jacket form an integral unit, and both an outlet of a first steam filling valve and an inlet of a first pressure sensor enter the heating part of the jacket, while both an outlet of a steam filling valve and an inlet of a second pressure sensor and an inlet of a third steam filling valve enter the sterilization chamber into which both an outlet of the third steam filling valve and an inlet of a third pressure sensor enter, enter the area of the filling part of the jacket.

5. The steam sterilizer jacket embedding the sterilization chamber according to claim 4, characterized in that the steam pressure in the sterilization chamber and the steam pressure in the filling part is, during a pressure rise in the sterilization chamber and during a sterilization exposure itself, higher than the steam pressure in the heating part.

* * * * *

UNITED STATES PATENT AND TRADEMARK OFFICE
CERTIFICATE OF CORRECTION

PATENT NO. : 7,645,429 B2  Page 1 of 1
APPLICATION NO. : 11/569962
DATED : January 12, 2010
INVENTOR(S) : Habrovec et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 335 days.

Signed and Sealed this

Sixteenth Day of November, 2010

David J. Kappos
*Director of the United States Patent and Trademark Office*